United States Patent [19]

Nilsson et al.

[11] Patent Number: 5,728,713

[45] Date of Patent: Mar. 17, 1998

[54] NEW USE OF QUINOLINE-3-CARBOXAMIDE COMPOUNDS

[75] Inventors: Bo Nilsson, Helsingborg; Agneta Svedberg; Per Gjörstrup, both of Lund, all of Sweden

[73] Assignee: Pharmacia & Upjohn, Stockholm, Sweden

[21] Appl. No.: 704,588

[22] PCT Filed: Mar. 8, 1995

[86] PCT No.: PCT/SE95/00244

§ 371 Date: Oct. 29, 1996

§ 102(e) Date: Oct. 29, 1996

[87] PCT Pub. No.: WO95/24195

PCT Pub. Date: Sep. 14, 1995

[30] Foreign Application Priority Data

Mar. 10, 1994 [SE] Sweden ................... 9400809

[51] Int. Cl.$^6$ .................................................. A61K 31/47
[52] U.S. Cl. .................................. 514/312; 514/311
[58] Field of Search ............................... 514/312, 311

[56] References Cited

U.S. PATENT DOCUMENTS

| | | | |
|---|---|---|---|
| 3,960,868 | 6/1976 | Ferrini et al. | 260/287 |
| 4,107,310 | 8/1978 | Allais et al. | 424/258 |
| 4,547,511 | 10/1985 | Eriksoo et al. | 514/312 |
| 4,738,971 | 4/1988 | Eriksoo et al. | 514/312 |
| 5,310,913 | 5/1994 | Gunnarsson et al. | 546/155 |

FOREIGN PATENT DOCUMENTS

| | | |
|---|---|---|
| 4323948 | 10/1968 | Japan . |
| 9015052 | 12/1990 | Japan . |
| 9112804 | 5/1991 | Japan . |
| 9114432 | 10/1991 | Japan . |
| 9204325 | 3/1992 | Japan . |
| 9207833 | 5/1992 | Japan . |
| 9216104 | 10/1992 | Japan . |
| 9306829 | 4/1993 | Japan . |

OTHER PUBLICATIONS

DiPiro et al., Pharmacotherapy, A Pathophysiologic Approach, pp. 447–449,1989.
Shridar et al., Indian Journal of Chemistry, 17B:488–490, 1979.
Carlsten, H., et al., APMIS, 97:728–732, 1989.
Cook, S.D., et al., Ann. Neurol., 22:634–638, 1987.
Coppola, G. M., et al., Organic Mag. Res., 17(9): 242–245, 1981.
Dhib–Jalbut, S., et al., Annal. Allergy, 64:433–444, 1990.
Fabian, W.M.F., et al., J. Med. Structure, 317:1–15, 1994.
Hauser, S.L., N. Eng. J. Med., 308:173–183, 1983.
Hirozumi, I., Chem. Abstracts, 116(23):85, 1992.
Kalland, T., et al., J. Immunol., 134:3956–3961, 1985.
Kalland, T., Cancer Res., 46:3018–3022, 1986.
Kalland, T., J. Immunol., 144:4472–6, 1990.
Kappos, L., Ann. Neurol., 23:56–63, 1988.
Karussis, D.M., Autoimmunity, 1992:101.

Karussis, D.M., J. Neurol., 1992, 239 (suppl 2):S96.
Karussis, D.M., Neurology, 42 (suppl 3):346, 1992.
Karussis, D.M., J. Neuroimmunol., 1991; 1 (suppl):159.
Larsson, E.L., et al., Int. J. Immunopharmacol., 9:425–431, 1987.
Mehta, P.J., Neurol., 32:372–77, 1982.
Myrianthopoulos, N.C., Handbook of Clinical Neurology, 3(47):289–317, 1985.
Oksenberg, J.R., et al., Nature, 345:344–347, 1990.
Patzold, U., et al., J. Neurolog. Sci., 54:377–394, 1982.
Prineas, J.W., Koetsier, J.C. (ed.) Handbook of Clinical Neurology, pp. 213–257, Elsevier Science Publ., Amsterdam, 1985.
Shridar, D.R., Sastry, C.V., Mehrotra, A.K., Indian Journal of Chemistry, 17B:488–490, 1979.
Tarkowski, A., et al., Arthr. Rheum., 29(11):1405–1409, 1986.

Primary Examiner—Marianne M. Cintins
Assistant Examiner—Dwayne C. Jones
Attorney, Agent, or Firm—Pravel, Hewitt, Kimball & Krieger

[57] ABSTRACT

Method of treating inflammatory bowel disease with a quinoline-3-carboxamide compound comprising

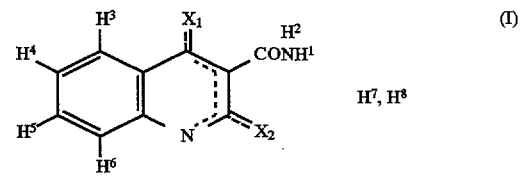

(I)

structure (I), optionally with substituents for the hydrogen atoms shown: ($H^{1-9}$), or a pharmaceutically acceptable salt of said compound where: (a) - - - represents that there are two conjugated double bonds between the atoms comprised by the dashed line; (b) $X_1$ and $X_2$ are separately selected from an oxygen atom or an $NH^9$ group, said $X_1$ and $X_2$ being bound by a single bond to the ring when attached to $H^7$ or $H^8$ and by a double bond when not bound to $H^7$ or $H^8$; (c) $H^{1-9}$ are hydrogens with the provision that $H^9$ is only present when at least one of $X_1$ and $X_2$ is the $NH^9$ group; (d) $H^7$ and $H^8$ are hydrogens that are attached to different atoms selected among $X_1$, $X_2$ and the nitrogen atom (N) in the quinoline ring, for the manufacture of a composition intended for treating inflammatory bowel disease or conditions associated with this disease. Also described are methods for treating inflammatory bowel disease or conditions associated with this disease in which methods the above compounds are administered to a living body. Particularly preferred compounds are N-phenyl-N-methyl-1,2-dihydro-4-hydroxy-1-methyl-2-oxo-quinoline-3-carboxamide or a salt thereof.

6 Claims, No Drawings

NEW USE OF QUINOLINE-3-CARBOXAMIDE COMPOUNDS

This application is a 371 of PCT/SE95/00244 filed on Mar. 8, 1995.

The present invention concerns the use of quinoline-3-carboxamide compounds, in particular roquinimex (Linomide®), or a pharmaceutically acceptable salt thereof for treating inflammatory bowel disease (IBD) including idiopathic ulcerative colitis (UC) and Crohn's disease.

BACKGROUND OF THE INVENTION

Inflammatory bowel disease (IBD) refers to both idiopathic ulcerative colitis (UC) and Crohn's disease. These are important chronic medical disorders of unknown etiology, characterized by symptoms of inflammation of the bowel with systemic response and also extraintestinal manifestations.

The cause of IBD is not known. The marked difference in incidence in ethnic groups and the tendency of IBD to cluster in families have suggested genetic or other host factors, but no consistent genetic markers have been found. No infectious agent has been consistently isolated. Emotional factors are probably not etiologic but they may exacerbate symptoms. The extraintestinal manifestations, the reported presence of antibodies to colonic epithelial cells and of cytotoxic T-cells and the clinical and histological response to immunosuppressive agents have suggested an immunological basis for the intestinal injury.

The incidence of UC in Scandinavia is 5 to 8 cases/100.000 inhabitants. The incidence of Crohn's disease is increasing but still a bit lower than in UC.

UC is confined to colon and rectum only. The cardinal symptoms of acute UC are diarrhea, rectal bleeding, fever, weight loss and abdominal pain. The disease can be mild but is also associated with complications such as toxic dilations of the colon and carcinoma of the colon. In Crohn's disease, the small intestine and the colon are most often affected, but any part of the gastrointestinal tract may be involved. The onset of symptoms are more subtle than in UC. The intestinal manifestations can for example be abdominal pain, diarrhea, fissures, fistulas, perirectal abscesses. Extraintestinal manifestations in common for IBD can for example be nutrional abnormalities, anemia, diseases of the skin (erythema nodosum), arthritis (anchylosing spondylitis) and hepatic and renal abnormalities.

This formula is a collective formula for the tautomeric structures II–IV.

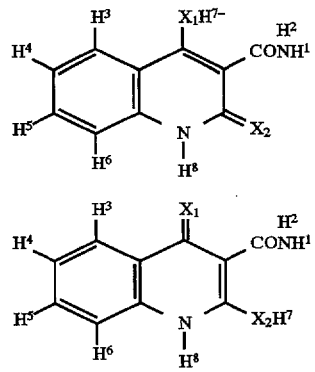

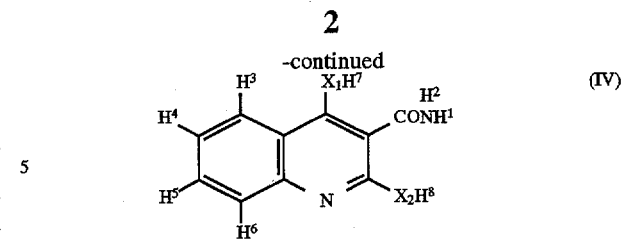

In formula I–IV:

(a) - - - represents that there are two conjugated double bonds between the atoms comprised by the dashed line (only formula I).

(b) $X_1$ and $X_2$ are separately selected from an oxygen atom or an $NH^9$ group that possibly is substituted, said $X_1$ and $X_2$ being bound by a single bond to the ring when attached to $H^7$ or $H^8$ and by a double bond when not bound to $H^7$ or $H^8$.

(c) $H^{1-9}$ are hydrogens, with the provision that $H^9$ is only present when at least one of $X_1$ and $X_2$ is the $NH^9$ group.

(d) $H^7$ and $H^8$ are hydrogens that are attached to different atoms selected among $X_1$, $X_2$ and the nitrogen atom in the quinoline ring said $X_1$ and $X_2$ being bound by a single bond to the ring when attached to $H^7$ or $H^8$ and by a double bond when not bound to $H^7$ or $H^8$.

The substituents that are to replace $H^{1-9}$ may, according to the prior art, comprise any substituent that gives compounds that can be isolated.

The medical treatment of both UC and Crohn's disease consists mainly of sulfasalazine and corticosteroids. Mild to moderate acute UC may respond to supportive measures supplemented by sulfasalazine alone. Sulfasalazine is split by bacterial action in the colon to yield sulfapyridine and 5-aminosalicylate, the latter considered to be active agent through its local inhibition of prostaglandine and leukotriene synthesis. If this regimen is insufficient, it can be supplemented by corticosteroid therapy, given either as oral prednisone or as hydrocortisone administered as a bedtime enema. Acute severe UC may lead to toxic megacolon, a medical emergency requiring systemic corticosteroids in large doses, coverage by broad spectrum antibiotics, and in some cases emergency colectomy. In Crohn's disease the medical treatment is similar to that for UC, with sulfasalazine and corticosteroids being the main agents used beyond supportive and dietary measures. Surgery is most frequently required in the case of obstruction, fistula formation or abscesses.

Quinoline-3-carboxamide compounds have been suggested as pharmaceuticals. The compounds have comprised the structure given in formula I below, optionally with substituents for the hydrogen atoms shown ($H^{1-9}$, where $H^9$ is part of $X_1$ or $X_2$ as shown in (b) below) and, where appropriate, salts of the compounds:

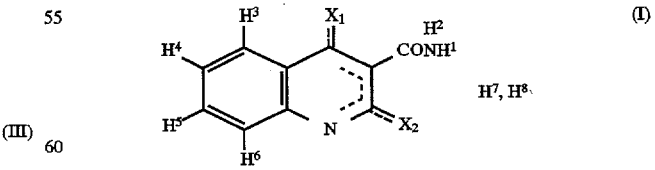

See for instance Indian Journal of Chemistry Vol 178 (1979) 488–90 (anti-inflammatory properties), U.S. Pat. No. 3,960,868 (=GB 1,467,061, analgesic, anticonceptive, anti-inflammatory and anti-allergic properties), U.S. Pat. Nos. 4,547,511 and 4,738,971 (enhancing cell-mediated immunity), WO 9015052 (=U.S. Ser. No. 651,234, filed May 31, 1990) (immunomodulator), U.S. Pat. No. 4,107,310 (analgetics) and JP 68023948 (bacteriocides). Patents and patent applications given above are hereby incorporated by reference. In general it can be stated that many of the compounds comprising structure I are classified as immune modulators with individual effects spanning the spectra from suppression to stimulation of the immune system. The specific effect achieved depends on the substituents.

One of the most important compounds with formula I are the 1,2-dihydro-hydroquinoline-3-carboxamides, particularly N-phenyl-N-methyl-1,2-dihydro-4-hydroxy-1-methyl-2-oxo-quinoline-3-carboxamide (roquinimex, trade mark Linomide®), i.e. structures I and II with a substituent for $H^1$ that equals phenyl, for $H^2$ that equals methyl, for $H^8$ that equals methyl (attached to the nitrogen atom of the quinoline ring), with no substituents for $H^{3-7}$, with $H^7$ attached to $X_1$, and with each of $X_1$ and $X_2$ equaling an oxygen atom. The compound has double bonds between positions 3 and 4 and between position 2 and $X_2$.

The scientific experimentation with roquinimex has shown that roquinimex has multiple immunological activities. It has thus been found that roquinimex increases the proliferative response to T and B cell mitogens [28], enhances antibody production [29] and augments NK cell activity [30, 31]. Moreover, its immunostimulating and immunoregulating properties may be useful in the treatment of tumors [32] and systemic lupus erythematosis [33, 34] as suggested in U.S. Pat. Nos. 4,547,511 and 4,738,971.

Published PCT-application WO 91/12804 discloses roquinimex as a drug for the treatment of retrovirus infections. WO 91/14432 discloses roquinimex as a drug for regenerating lymphoid cells in patients treated with autologous bone marrow transplantation. WO 93/06829 discloses roquinimex as a drug for the treatment of multiple sclerosis. These published patent applications are hereby incorporated by reference.

Quinoline-3-carboxamide compounds according to the present invention are hitherto not known for treating inflammatory bowel disease (IBD). WO92/07833 (POLLAK) discloses dihydroquinoline derivatives which may be used for treating IBD. Anyhow WO92/07833 only teaches compounds with two quinoline rings, while the compounds according to the present application has one ring. Furthermore the compounds according to WO92/07833 lack the carboxamide structure which is an essential characteristic of the compounds in the present application. WO92/04325 discloses naphtalenepropionic acid derivatives which may be used for treating IBD. Anyhow the quinoline ring according to WO92/04325 is in the form of a 2-quinolinylmetoxy group which totally lacks the characteristic substitution pattern of the compounds according to the present invention.

SUMMARY OF THE INVENTION

According to the present invention it has now surprisingly been shown that treatment with quinoline-3-carboxamide compounds, in particular roquinimex (Linomide®), or a pharmaceutically acceptable salt thereof for treating inflammatory bowel disease (IBD) including idiopathic ulcerative colitis (UC) and Crohn's disease and conditions associated with IBD.

Roquinimex may be used as such or as a pharmaceutically acceptable salt thereof. Furthermore, roquinimex can be used in combination with other agents. Formulations that could be used according to the present invention are disclosed in U.S. Pat. No. 4,547,511 col. 11.

Some of the most frequent adverse events seen during treatment with roquinimex are symptoms probably related to an enhanced activation of the immune system as they are similar to the symptoms of vital infections. The symptoms are muscle and joint pain and stiffness and joint inflammation. In view of these facts that roquinimex has shown to stimulate the immune response in different experimental and clinical studies which also has lead to an adverse event profile of general musculoskeletal discomfort, it could not be expected that roquinimex could show effect on inflammatory bowel disease (IBD).

OBJECTIVES OF THE INVENTION

One major objective of the invention is to provide a method for treating inflammatory bowel disease (IBD) including idiopathic ulcerative colitis (UC) and Crohn's disease or conditions associated with IBD with quinoline-3-carboxamide compounds, in particular roquinimex (Linomide®), or a pharmaceutically acceptable salt thereof.

Further objectives are to provide drugs to be used for the manufacture of pharmaceutical compositions for the treatment of the conditions given in the preceding sentence.

Other objectives of the invention will become apparent to one skilled in the art, and still other objectives will become apparent hereinafter.

EXAMPLE 1

One patient with ulcerative proctitis (ulcerative colitis of the rectum) has so far been subjected to long term treatment with roquinimex. The patient received his diagnosis ulcerative proctitis in 1965. In 1983 he got renal cancer. In spite of treatment with medroxiprogesteron and interferon alpha his renal cancer progressed. In May 1988 he started treatment with roquinimex in a phase I-study. Roquinimex was given in an oral solution once a week with escaling doses, 0.05–0.6 mg/kg. His ulcerative proctitis was at that time treated with sulfasalazine (Salazopyrin®). During roquinimex treatment his ulcerative proctitis improved and the dose of sulfasalazine was decreased after about five weeks. End of July 1988 he resumed treatment with roquinimex with a dose of 15 mg twice weekly in a phase II study in patients with renal cell carcinoma. About two months later there were no clinical signs or symptoms of his ulcerative proctitis and treatment with sulfasalazine was withdrawn.

He received later a complete response of his renal cancer. The roquinimex treatment was terminated in March 1992 and he is at this date still in complete remission both with respect to the ulcerative proctitis and his renal cancer.

We claim:

1. A method for treating a patient suffering from, or at risk for acquiring, inflammatory bowel disease, comprising administering to the patient an effective therapeutic dose of N-phenyl-N-methyl-1,2-dihydro-4-hydroxy-1-methyl-2-oxo-quinoline-3-carboxamide or tautomers thereof, or a pharmaceutically acceptable salt thereof.

2. The method of claim 1, wherein the compound is administered orally.

3. The method of claim 1, whereby said compound is administered by injection.

4. The method of claim 1, whereby said compound is administered parenterally.

5. The method of claim 1, 2, 3, or 4, wherein the effective amount is from about 0.01 to about 10 mg/kg body weight and the amount is administered from once daily to once every two weeks.

6. The method of claim 5, wherein the effective amount is from about 0.05 to about 1 mg/kg body weight.

* * * * *